United States Patent [19]

Kitagawa et al.

[11] Patent Number: 5,268,390
[45] Date of Patent: Dec. 7, 1993

[54] METHOD FOR PREVENTITNG THE GROWTH OF MICROORGANISMS IN CITRUS FRUITS

[75] Inventors: Hirotoshi Kitagawa, Kida; Ryoji Kitahata, Kodoma; Buhei Kohno, Uji; Yasushi Sekiyama, Nishinomiya; Yuichi Mizukami, Kobe, all of Japan

[73] Assignees: The Green Cross Corporation; Kabushiki Kaisha Daikei, both of Osaka, Japan

[21] Appl. No.: 889,224

[22] Filed: May 27, 1992

[30] Foreign Application Priority Data

May 31, 1991 [JP] Japan .................. 3-229825

[51] Int. Cl.$^5$ ............................. A01N 47/46
[52] U.S. Cl. .................................... 514/514
[58] Field of Search ............................ 514/514

[56] References Cited

FOREIGN PATENT DOCUMENTS 43-14823  6/1968  Japan ..................... 514/514
473769   10/1937  United Kingdom ........ 514/514

OTHER PUBLICATIONS

"Inhibitory Effect of Volatile Constituents of Plants on the Proliferation of Bacteria", J. Antibact. Antifung. Agents, vol. 11, No. 11, pp. 609–615, 1983.

"Antifungal Activity of Powdery Black Mustard, Powdery Wasabi (Japanese Horseradish), and Allyl Isothiocyanate by Gaseous Contact", J. Antibact. Antifung. Agents, vol. 13, No. 5, pp. 199–204, 1985 (Goi et al).

Primary Examiner—Allen J. Robinson
Attorney, Agent, or Firm—Jordan and Hamburg

[57] ABSTRACT

An excellent method for preventing the growth of microorganisms in citrus fruits without causing phytotoxicity, taste disorder and pericarp disorder is provided by contacting the citrus fruits for a short time with a high concentration of gaseous isothiocyanate having a fungicidal effect against *Penicillium digitatum* and *Geotrichum candidum*.

2 Claims, No Drawings

METHOD FOR PREVENTITNG THE GROWTH OF MICROORGANISMS IN CITRUS FRUITS

BACKGROUND OF THE INVENTION

1. Field of the Invention

The present invention relates to a method for preventing the growth of microorganisms in citrus fruits.

2. The Prior Art

Generally, fruits are liable to degradation and corruption by various fungi, particularly *Penicillium digitatum* or *Geotrichum candidum*, during transportation or storage thereof. Especially, imported citrus fruits, such as, lemons, oranges and grapefruits are sometimes corrupted by 30% or more or the total imported amount during the season of May through July, and the discarding treatment of corrupted fruits has recently become even a social problem.

Heretofore, in order to cope with such discarding, various antimicrobial agents have been developed and used to protect citrus fruits from microorganisms.

Meanwhile, in order to keep fruits fresh, a method has also been attempted of treating the fruits by preservatives supported on a porous material like activated charcoal or zeolite.

However, each of the above conventional treating methods have problems as well as advantages. Particularly, phytotoxicity caused on the fruits when a drug is used can not be disregarded, so that the usage of a chemical has to be restricted from the viewpoints of agricultural chemicals.

SUMMARY OF THE INVENTION

An object of the present invention is to obviate the above problems.

The present invention is a method for preventing the growth of microorganisms in citrus fruits by contacting the citrus fruits with gaseous isothiocyanate for a short treating time, the isothiocyanate being used in such a high concentration that exhibits fungicidal effect against *Penicillium digitatum* and *Geotrichum candidum* but does not incur phytotoxicity, taste disorder and pericarp disorder. More concretely, the present invention is a method for protecting citrus fruits from microorganisms by contacting the citrus fruits with gaseous isothiocyanate of a concentration of 1,000–3,000 ppm for 120–300 sec.

Namely, the present method uses innoxious isothiocyanate. For example, the present invention is a method for protecting citrus fruits from microorganisms by contacting the citrus fruits with gaseous allyl isothiocyanate for a short treating time, the allyl isothiocyanate being used in such a high concentration that exhibits fungicidal effect against *Penicillium digitatum* and *Geotrichum candidum* but does not incur phytotoxicity, taste disorder and pericarp disorder. Therefore, superior effects were obtained of preventing the growth of *Penicillium digitatum* and *Geotrichum candidum* and further of preventing phytotoxicity, taste disorder and pericarp disorder of the citrus fruits.

Particularly, by contacting citrus fruits with a high concentration of gaseous allyl isothiocyanate for a short time, a remarkably distinct difference of effect in preventing the taste disorder was attained as compared with a case, for example, of treating the citrus fruits for a long time with allyl isothiocyanate spontaneously evaporated from a solid preparation comprising allyl isothiocyanate as a main component.

Thus, according to the present invention, all the problems of fungicidal effect, phytotoxicity, taste disorder and pericarp disorder, etc., can be solved, so that the present invention also has the advantage of disposing with the conventional social problems of a considerable percentage of corruption of imported citrus fruits and the discarding of the corrupted citrus fruits.

DETAILED DESCRIPTION OF THE PREFERRED EMBODIMENTS

Hereinafter, the present invention will be explained in more detail with reference examples.

EXAMPLE 1

This example is an embodiment of a method for protecting oranges taken as an example of citrus fruits from microorganisms.

As a chemical to be contacted in a gas phase with citrus fruits, use was made of allyl isothiocyanate as an example of isothiocyanate.

Gaseous allyl isothiocyanate of a concentration of 2,000 ppm was contacted with the oranges for a treating time of 180 sec.

In order to ascertain the effects of protecting the oranges from microorganisms, the following 3 types of comparative examples were effected.

COMPARATIVE EXAMPLE 1

Allyl isothiocyanate of a concentration of 500 ppm was used for a treating time of 30 sec.

COMPARATIVE EXAMPLE 2

Allyl isothiocyanate of a concentration of 500 ppm was used for a treating time of 180 sec.

COMPARATIVE EXAMPLE 3

Allyl isothiocyanate of a concentration of 2,000 ppm was used for a treating time of 30 sec.

Concretely, the following test was performed on the aforementioned Example 1 and Comparative Examples 1–3.

Test Method

As citrus fruits, navel oranges harvested in U.S.A. were used.

At first, the pericarps of the fruits were scarred at 4 points and inoculated with *Penicillium digitatum* or *Geotrichum candidum* which is a major pathogen of citrus fruits.

The thus inoculated navel oranges were treated or contacted with gaseous allyl isothiocyanate in a chamber (not shown in a drawing) under the respective conditions of Example 1 and Comparative Examples 1–3.

The thus inoculated and treated navel oranges were classified into 4 types, each type consisting of 3 oranges, and put in polyethylene film bags of a thickness of 0.02 mm to observe the state of the fruits respectively of Example 1 and Comparative Examples 1–3.

Test Results (A) The navel oranges of Comparative Examples 1–3 inoculated with *Penicillium digitatum* showed sporulation all over the fruits. However, those of Example 1 did not show substantial sporulation, though some of them showed phytotoxicity.

(B) The navel oranges of Comparative Examples 1-3 inoculated with *Geotrichum candidum* showed the so-called "water rotting" of a diameter of 10 mm or more. In contrast, those of Example 1 showed "water rotting" of a diameter of not more than 5 mm.

(C) The navel oranges tested in Example 1 did not show phytotoxicity, taste disorder and the residual odor, despite the high concentration of the used allyl isothiocyanate and the long treating time as compared with those of Comparative Examples 1-3.

REFERENTIAL EXAMPLE

In order to ascertain the effect of treating the citrus fruits with gaseous isothiocyanate for a short time as in Example 1, a referential test example was performed wherein the citrus fruits were contacted for a long time with gaseous allyl isothiocyanate spontaneously evaporated from a solid preparation consisting mainly of allyl isothiocyanate.

Test Samples

The following 7 types of separated packages of solid preparation of allyl isothiocyanate were prepared as test samples, and each package was adhered on the inner side of a bag of ethylene/vinyl alcohol copolymer resin. Then, each 4 oranges were put in each bag. As a control test sample bags each containing 4 oranges without containing the package were prepared.

(A) 2.8 mg/bag
(B) 7.2 mg/bag
(C) 14.4 mg/bag
(D) 21.0 mg/bag
(E) 50.0 mg/bag
(F) 100.0 mg/bag
(G) 150.0 mg/bag The numerical values of the above (A)-(G) are expressed as mg of allyl isothiocyanate contained in the solid preparation.

Four bags each were prepared of the 8 groups of the above (A)-(G) and the control test sample.

Storing Condition

The above samples were kept at 8° C. for 15 days. Any change, such as, growth of fungi, was not observed at this stage, so that the samples were left for an additional week at an elevated temperature of 28° C.

Test Results

After the test, the oranges were observed on the state of damage, growth of fungi at the pericarps, and expansion of the bags, respectively.

The results are shown in the following Tables 1-1 and 1-2.

TABLE 1-1

| Sample | Change of State | After 2 days | After 4 days ① | ② | ③ | ④ | After 7 days ① | ② | ③ | ④ | AIT Gas Concentration (ppm) |
|---|---|---|---|---|---|---|---|---|---|---|---|
| Control | Expansion | Δ | Δ | Δ | ○ | Δ | X | X | X | X | 0 |
|  | Damage | — | — | — | — | — | ± | + | ± | ± |  |
|  | Growth of Fungi | — | — | — | — | — | — | — | — | — |  |
| A | Expansion | Δ | ○ | Δ | ○ | Δ | ○ | X | ○ | X | 8.9 |
|  | Damage | — | — | — | — | — | — | ± | — | ± |  |
|  | Growth of Fungi | — | — | — | — | — | — | — | — | — |  |
| B | Expansion | Δ | Δ | ○ | Δ | Δ | Δ | ○ | Δ | X | 10.9 |
|  | Damage | — | ± | — | ± | — | ○ | — | ○ | ○ |  |
|  | Growth of Fungi | — | — | — | — | — | — | — | — | — |  |
| C | Expansion | Δ | ○ | Δ | ○ | ○ | ○ | X | X | X | 8.9 |
|  | Damage | — | — | — | — | — | — | — | — | — |  |
|  | Growth of Fungi | — | — | — | — | — | — | — | — | — |  |

AIT is an abbreviation of allyl isothiocyanate.

TABLE 1-2

| Sample | Change of State | After 2 days | After 4 days ① | ② | ③ | ④ | After 7 days ① | ② | ③ | ④ | AIT Gas Concentration (ppm) |
|---|---|---|---|---|---|---|---|---|---|---|---|
| D | Expansion | Δ | Δ | ○ | ○ | ○ | Δ | X | X | X | 13.5 |
|  | Damage | — | — | — | — | — | — | ± | + | — |  |
|  | Growth of Fungi | — | — | — | — | — | — | — | — | — |  |
| E | Expansion | Δ | ○ | ○ | ○ | ○ | ○ | ○ | ○ | ○ | 14.6 |
|  | Damage | — | — | — | — | — | — | — | — | — |  |
|  | Growth of Fungi | — | — | — | — | — | — | — | — | — |  |
| F | Expansion | Δ | ○ | ○ | Δ | Δ | ○ | ○ | ○ | ○ | 23.9 |
|  | Damage | — | — | — | — | — | — | — | — | — |  |
|  | Growth of Fungi | — | — | — | — | — | — | — | — | — |  |
| G | Expansion | Δ | Δ | Δ | Δ | Δ | ○ | ○ | ○ | ○ | 34.7 |
|  | Damage | — | — | — | — | — | — | — | — | — |  |
|  | Growth | — | — | — | — | — | — | — | — | — |  |

TABLE 1-2-continued

| Sample | Change of State of Fungi | Storage Period (Days after Elevation of Temperature to 28° C.) | | | | | | | | AIT Gas Concentration (ppm) |
|---|---|---|---|---|---|---|---|---|---|---|
| | | After 2 days | After 4 days ① | ② | ③ | ④ | After 7 days ① | ② | ③ | ④ | |

AIT is an abbreviation of allyl isothiocyanate.

In the above Tables 1-1 and 1-2, the symbols used denote the following.

Expansion:
(−) no expansion was observed.
(Δ) a little expansion was observed.
(○) considerable expansion was observed.
(×) damage of the bag due to expansion was observed.

Damage:
(−) no damage was observed.
(±) slight damage was observed.
(+) minor damage was observed.
(◯) major damage was observed.

Growth of Fungi:
(−) growth of fungi was not observed.
(+) growth of fungi was observed.

The encircled numerals ①-④ are Nos. of the tested bags.

After 2 days of the temperature elevation, no difference was observed between the tested bags, so that the above results were not shown on each tested bag.

As seen from the above Tables 1-1 and 1-2, growth of fungi was not observed and the other extraordinary states were not observed on all the tested oranges of (A)–(G) and the control test after storage at 8° C. for 2 weeks.

However, after elevation of the storing temperature to 28° C., the oranges treated with a low concentration of (A)-(D) of AIT or those of the control sample showed remarkable corruption and a somewhat blackened appearance. On the other hand, the oranges treated with a high concentration of (E)-(G) of AIT showed sound colored appearance without showing corruption.

However, when the tested oranges treated with a high concentration of (E)-(G) of AIT were severed, they smelled like Japanese horseradish, and juice thereof gave an irritating itching taste.

Consideration of the Test Results

From the above results, the following considerations are derived.

(1) When gaseous allyl isothiocyanate is not more than a certain concentration, corruption and damage of the fruits can not be prevented.

(2) Meanwhile, when the gaseous allyl isothiocyanate is more than a certain concentration, corruption and damage of the fruits can be prevented, although a noticeable taste disorder is observed. This is presumed due to permeation of allyl isothiocyanate into the interior of the oranges through the pericarp as a result of prolonged contact of the fruits with allyl isothiocyanate.

(3) Pericarp disorder was not observed in any of the tested oranges. This is presumed due to the strong resistance of the fruits harvested at the season to the pericarp disorder in addition to no growth of fungi.

However, seeing no growth of fungi on the oranges of the control group, it can not be concluded that the allyl isothiocyanate of the test groups have fungicidal effect.

(4) Considering the aforedescribed points, contradictory problems arise that when treating oranges with allyl isothiocyanate for a long time as in the Referential Example, corruption and damage of the fruits are unavoidable if the concentration of allyl isothiocyanate is low, while taste disorder occurs if the concentration of allyl isothiocyanate is higher than a certain level.

(5) In contrast, the oranges of Example 1 were treated with a high concentration of allyl isothiocyanate for a short time, so that taste disorder was not observed and corruption, etc., of the fruits were prevented. Therefore, the above contradictory problems as in the Referential Example can be solved simultaneously.

OTHER EXAMPLES

Though the concentration of allyl isothiocyanate of 2,000 ppm was used in the above Example 1, the concentration of allyl isothiocyanate is not limited solely thereto and can be varied. However, the concentration is preferably in a range of 1,000–3,000 ppm.

Though the treating time of 180 sec was used in Example 1, the treating time is also not restricted thereto and can be varied. However, the treating time is preferably in a range of 120–300 sec.

Summing up, what is necessary is to contact citrus fruits for a short time with a high concentration of gaseous allyl isothiocyanate that exhibits fungicidal effect against *Penicillium digitatum* or *Geotrichum candidum* but does not cause phytotoxicity, taste disorder and pericarp disorder to citrus fruits.

As allyl isothiocyanate, use may be made of any natural or synthetic allyl isothiocyanate. Allyl isothiocyanate is not restricted solely to a single solid preparation consisting of 100% of allyl isothiocyanate, and a mixture oil containing allyl isothiocyanate, an extract of mustard or Japanese horseradish(usually contains about 90% of allyl isothiocyanate), or a crude product may be used.

However, because the present invention aims to protect citrus fruits from microorganisms, natural allyl isothiocyanate is preferably used from a viewpoint of agricultural chemicals.

Though allyl isothiocyanate was used as a drug which was to be contacted in a gas phase with oranges, other isothiocyanates having a substituent other than the allyl group can also be used. What is necessary is to use an ester of isothiocyanic acid.

Although the present invention has been explained with specific examples and numerical values, it is of course apparent to those skilled in the art that various changes and modifications thereof are possible without departing from the broad spirit and scope of the present invention as defined in the appended claims.

What is claimed is:

1. A method for preventing the growth of at least one of *Penicillium digitatum* and *Geotrichum candidum* on citrus fruits comprising contacting the citrus fruits with gaseous allyl isothiocyanate of a concentration of 1,000–3,000 ppm for 120–300 seconds, the isothiocyanate being used in such a high concentration that exhibits fungicidal effect against at least one of *Penicillium digitatum* and *Geotrichum candidum* but does not incur phytotoxicity, taste disorder and pericarp disorder.

2. The method of claim 1, wherein the allyl isothiocyanate is spontaneously evaporated from a solid preparation comprising allyl isothiocyanate as a main component.

* * * * *